(12) United States Patent
Busch et al.

(10) Patent No.: US 9,174,914 B2
(45) Date of Patent: Nov. 3, 2015

(54) NANOSCALE β-NUCLEATING AGENT FOR POLYPROPYLENE

(75) Inventors: Detlef Busch, Saarlouis (DE); Dominic Klein, Bexbach (DE); Bertram Schmitz, Sarreguemines (FR)

(73) Assignee: Treofan Germany GmbH & Co. KG (DE)

( * ) Notice: Subject to any disclaimer, the term of this patent is extended or adjusted under 35 U.S.C. 154(b) by 737 days.

(21) Appl. No.: 13/501,796

(22) PCT Filed: Oct. 13, 2010

(86) PCT No.: PCT/EP2010/006240
§ 371 (c)(1),
(2), (4) Date: Apr. 13, 2012

(87) PCT Pub. No.: WO2011/047797
PCT Pub. Date: Apr. 28, 2011

(65) Prior Publication Data
US 2012/0202905 A1    Aug. 9, 2012

(30) Foreign Application Priority Data
Oct. 20, 2009  (DE) .......................... 10 2009 050 439

(51) Int. Cl.
| | | |
|---|---|---|
| C08L 23/12 | (2006.01) |
| C08K 5/098 | (2006.01) |
| C07C 51/41 | (2006.01) |
| B01D 67/00 | (2006.01) |
| B01D 69/02 | (2006.01) |
| B01D 71/26 | (2006.01) |
| B29C 55/00 | (2006.01) |
| B82Y 30/00 | (2011.01) |
| C08J 3/20 | (2006.01) |
| C08J 3/205 | (2006.01) |
| C08J 5/18 | (2006.01) |
| C08J 9/00 | (2006.01) |
| C08K 5/00 | (2006.01) |
| H01M 2/14 | (2006.01) |
| H01M 2/16 | (2006.01) |
| B29C 55/12 | (2006.01) |
| B29K 23/00 | (2006.01) |
| B29K 105/04 | (2006.01) |

(52) U.S. Cl.
CPC .......... *C07C 51/412* (2013.01); *B01D 67/0027* (2013.01); *B01D 69/02* (2013.01); *B01D 71/26* (2013.01); *B29C 55/005* (2013.01); *B82Y 30/00* (2013.01); *C08J 3/201* (2013.01); *C08J 3/205* (2013.01); *C08J 5/18* (2013.01); *C08J 9/0052* (2013.01); *C08K 5/0083* (2013.01); *C08K 5/098* (2013.01); *H01M 2/145* (2013.01); *H01M 2/16* (2013.01); *B01D 2325/02* (2013.01); *B01D 2325/20* (2013.01); *B29C 55/12* (2013.01); *B29K 2023/12* (2013.01); *B29K 2105/04* (2013.01); *C08J 2323/10* (2013.01)

(58) Field of Classification Search
CPC ......... C07C 51/412; C08J 3/201; C08J 3/205; C08J 5/18; C08J 9/0052; C08J 2323/10; C08K 5/0083; C08K 5/098
USPC .................................... 521/79, 92, 93, 97, 1
See application file for complete search history.

(56) References Cited

U.S. PATENT DOCUMENTS

| | | | |
|---|---|---|---|
| 3,540,979 A | 11/1970 | Hughes et al. | |
| 2002/0137851 A1* | 9/2002 | Kim et al. | ..... 525/240 |
| 2008/0044617 A1 | 2/2008 | Schmitz et al. | |

FOREIGN PATENT DOCUMENTS

| | | | |
|---|---|---|---|
| DE | 3610644 A1 | | 10/1986 |
| DE | 4420989 A1 | | 12/1995 |
| DE | 102005025719 A1 | | 12/2006 |
| DE | 102008061748 A1 | | 6/2010 |
| EP | 0557721 A2 | | 9/1993 |
| EP | 1291380 | * | 12/2013 |
| WO | WO-02081557 A1 | | 10/2002 |

OTHER PUBLICATIONS

Zhang, et al., "Preparation and Characteristics of Nano-CaCO$_3$ Supported β-Nucleating Agent of Polypropylene", European Polymer Journal, vol. 44, (2008), pp. 1955-1961.
International Search Report for PCT/EP2010/006240 mailed Mar. 3, 2011.
International Preliminary Report on Patentability from PCT/EP2010/006240 dated May 8, 2012.

* cited by examiner

*Primary Examiner* — Irina S Zemel
(74) *Attorney, Agent, or Firm* — Drinker Biddle & Reath LLP

(57) ABSTRACT

The invention relates to a method for producing a dispersion of nanoscale dicarboxylic acid salts, to the use of these dispersions for producing a compound, and to the use for producing films. The invention further relates to the use of the compounds for producing films.

29 Claims, 2 Drawing Sheets

NANOSCALE β-NUCLEATING AGENT FOR POLYPROPYLENE

CROSS-REFERENCE TO RELATED APPLICATIONS

This application is a national stage application (under 35 U.S.C. §371) of PCT/EP2010/006240, filed Oct. 13, 2010, which claims benefit of German application 10 2009 050 439.7, filed Oct. 20, 2009.

The invention relates to a nanoscale β-nucleating agent for polypropylene, as well as a method for increasing the portion of the β-crystal modification in polypropylene, as well as a porous film.

Beside the amorphous phase, three different crystalline ones, the α-, β- and γ-phases, are known of polypropylene. Upon cooling polypropylene melts, usually α-crystalline PP is predominantly formed. With a certain temperature control during cooling of a polypropylene melt, an increased portion of the β-crystalline phase can be generated. The portion of β-crystalline PP generated in this manner amounts to less than 10% (1st heating). The hexagonal β-modification of the PP compared to the monocline α-modification is characterized by better mechanical properties, e.g. better impact strength and stress cracking resistance. Besides that, with 140-155° C., the β-modification of polypropylene has a clearly lower melting point compared to the α-modification with a melting point of at least 160° C. Therefore, in a number of applications, an increased portion of β-crystalline PP has a beneficial effect on certain performance characteristics of the polypropylene. For this reason, additives were developed in the past, which upon cooling of a melt result in high portions of polypropylene in the β-modification, so-called β-nucleating agents or β-nucleators.

In the German Patent 1188278, the pigment γ-quinacridone is described as a β-nucleator with high activity. The disadvantage of this nucleating agent, however, is the intensive red coloring and the lack of thermal stability. In U.S. Pat. No. 3,540,979, the calcium salt of phthalic acid is described as a thermally stable nucleating agent. The disadvantage of this nucleating agent is its low activity. The portion of β-crystalline PP achieved therewith amounts to 70% (K~0.5-0.7) at most.

A two-component nucleating system of calcium carbonate and organic dicarboxylic acids is described in DE 3 610 644. In practice, however, this nucleating system shows variable activity. Direct use of the calcium salts of the dicarboxylic acids described in DE 3 610 644 has been described in DE 4 420 989. The β-nucleating effect of various dicarboxamides, in particular N,N-dicyclohexyl-2,6-naphtalene-dicarboxamides, is described in EP 0557721. The disadvantages of this nucleator are high educt costs, as well as complicated synthesis steps during production.

The object of the present invention was to provide an improved β-nucleating agent, as well as a method for producing β-crystalline polypropylene, as well as an improved method for producing a film with high gas permeability. Using this method, it is to be possible to achieve high β-portions in a reproducible and reliable manner. The method is to be simple and efficiently performable. The modification with a β-nucleating agent must not impair the usual important performance characteristics of the polypropylene. The operational reliability upon producing porous films is to be improved.

This object is solved with a method for producing a stable dispersion of a non-aqueous, liquid phase and dispersed alkaline earth dicarboxylic acid salts, in which an aliphatic dicarboxylic acid is reacted with alkaline earth salt in an aqueous solution into an alkaline earth dicarboxylic acid salt, and the alkaline earth dicarboxylic acid salt is subsequently separated and dried, wherein this dried dicarboxylic acid salt is suspended and disintegrated in a non-aqueous, liquid phase, until a stable dispersion is formed.

Dispersion shall in terms of the present invention mean a heterogeneous mixture, in which the dicarboxylic acid salt is present as a solid in the continuous liquid phase finely distributed as the disperse phase, wherein the salt is not or hardly dissolved in the liquid phase. The two phases also do not form a chemical compound.

The dispersion is also characterized by the fact that the individual phases are separated from one another, i.e. are not dissolved in one another, and can be separated from one another again with physical methods, e.g. filtration, centrifugation. The stable dispersion substantially does not separate anymore by itself, for example by sedimentation.

A non-aqueous phase shall in terms of the present invention mean an organic compound, which is liquid at room temperature, and the water content of which amounts to <1 wt %, for example alcohols, lower alkanes, ketones, and similar liquids.

Drying, depending on the given context, shall in terms of the present invention mean the removal of water or moisture as well as the separation of the non-aqueous, liquid phase.

This object is also solved by a method for producing a compound of polypropylene and nanoscale dicarboxylic acid salt, wherein the non-aqueous, liquid phase is removed from the dispersion produced according to any of claims 1 to 6, the remaining powder of dicarboxylic acid salt is admixed with polypropylene in the form of powder or granulate, and subsequently the pre-mixture thus obtained is molten and extruded into a granulated compound.

Compound shall in terms of the present invention mean a homogeneous mixture of at least one polypropylene and dicarboxylic acid salt as an additive.

The object is likewise solved by a method for producing a compound of polypropylene and nanoscale dicarboxylic acid salt, in which a dispersion produced according to any of claims 1 to 6 is admixed with polypropylene in the form of powder or granulate, the non-aqueous phase is removed from this mixture, and subsequently the pre-mixture thus obtained is molten and extruded into a granulated compound.

Finally, the object is also solved by a method for producing a polypropylene with an increased portion of β-crystalline polypropylene, in which a compound, produced according to a method according to claim 7 or 8, as necessary mixed with a further polypropylene and/or additional polymers and/or further additives, is molten at a temperature of at least 150° C. and subsequently cooled such that the cooled polypropylene melt has an increased portion of β-crystalline polypropylene; as well as by a method for producing a biaxially stretched polypropylene film with at least one porous layer, in which a compound, produced according to a method according to claim 7 or 8, as necessary mixed with a further polypropylene and/or additional polymers and/or further additives, is molten at a temperature of at least 150° C. and extruded or co-extruded through a flat nozzle and cooled on cooling rollers such that the cooled pre-film has an increased portion of β-crystalline polypropylene, and the pre-film is subsequently heated and stretched in longitudinal direction and in transverse direction, and wherein the temperature during longitudinal stretching is selected such that the β-crystalline polypropylene of the pre-film is converted into the alpha-modification of the polypropylene.

The dependent claims describe preferred embodiments of the invention.

Figure 1:
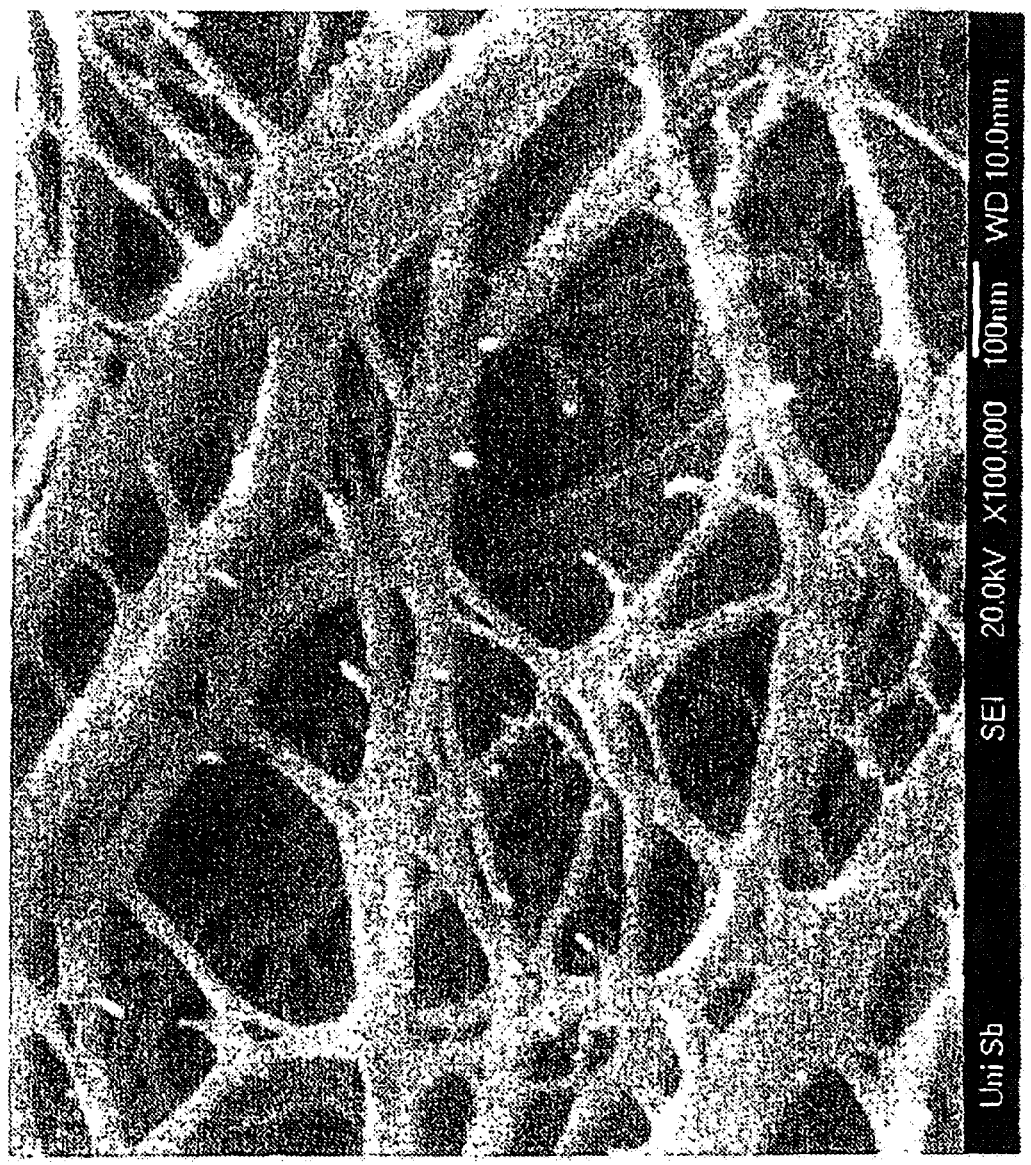
FIG. 1 shows a uniform distribution of the Ca-pimelate without agglomerates in the porous film.

The present invention is based on the discovery that nanoscale dicarboxylic acid salts, upon cooling of a polypropylene melt containing these nanoscale dicarboxylic acid salts, result in the formation of a high portion of β-crystalline polypropylene (hereinafter also β-portion). The cooled melt with a high β-portion forms a transparent PP matrix, since the particle size of the nanoscale dicarboxylic acid salts is considerably smaller than the wavelength of visible light. Nanoscale dicarboxylic acid salts in general have a particle size of 1 to 500 nm, preferably 5 to 300 nm, wherein simultaneously particles or agglomerates with a particle size of >1 µm are contained at less than 3%, preferably >0 to <1%. Thus, the mean particle size of the nanoscale dicarboxylic acid salts, too, lies within said range of 1 to 500 nm, preferably 5 to 300 nm.

Nanoscale dicarboxylic acid salts shall in terms of the present invention comprise salts, the aliphatic dicarboxylic acid they are based on has at least 4 to 15 C-atoms, in particular 5 to 10 C-atoms. Particularly preferred are salts of pimelic acid or suberic acid, for example Ca-pimelate or Ca-suberate. Mixtures of various dicarboxylic acid salts may also be used. In general, alkaline earth salts are preferred, however, in principle, other divalent metal salts, for example based on divalent iron, nickel, zinc, etc., may also be used.

The synthesis of the nanoscale dicarboxylic acid salts takes place via the per se known precipitation reaction of the aliphatic dicarboxylic acids, e.g. pimelic acid or suberic acid, with divalent metal salts, like for example chlorides, carbonates or hydroxides, preferably alkaline earth salts, like for example alkaline earth chloride, alkaline earth carbonate or alkaline earth hydroxide in aqueous solution. Alkaline earth hydroxides, like e.g. $Ca(OH)_2$, are preferred, since the formation of hydrochloric acid or $CO_2$ as a byproduct is avoided. For the reaction, in general, an aqueous solution of the aliphatic dicarboxylic acid is used. The aliphatic dicarboxylic acid is put into water and heated under stirring, until the aliphatic dicarboxylic acid has dissolved, for example at a temperature of 70 to 95° C., preferably 75 to 90° C. Subsequently, an aqueous metal salt solution, preferably alkaline earth salt solution, in particular a $Ca(OH)_2$ solution, is added under stirring. In that, the reactants are used in stoichiometric amounts. In that, the dicarboxylic acid salt precipitates as a fine precipitate. This precipitate sediments, is separated and dried with suitable methods, e.g. pre-dried in a drying cabinet, at 100-120° C. Subsequently, for example under vacuum, e.g. in a vacuum drying cabinet, at approx. 150 to 200° C., the residual moisture content of the dicarboxylic acid salt is further reduced. Preferably, the water content of the dried dicarboxylic acid salt amounts to 0-2 wt %, preferably >0 to 1 wt %. In this manner, a dry powdery dicarboxylic acid salt is obtained. Following drying, this powder contains agglomerates with a particle size of 1 to more than 100 µm, wherein the predominant portion of these agglomerates has a particle size of about 10 µm. The portion of these agglomerates in general lies above 5%.

According to the invention, in a next step, the dicarboxylic acid salt is suspended in an anhydrous liquid phase. The water content of the liquid phases in general lies below 1 wt %, preferably >0 to <0.8 wt %. The liquid phase is, for example, a lower alkane, which is liquid at room temperatures, e.g. hexane, heptane, or an alcohol, e.g. ethanol, butanol or isopropanol or liquid ketone, e.g. acetone. Mixtures of these liquid phases may also be used. In general, at least 5 up to 60 wt %, preferably 10 to 50 wt %, in particular 15 to 40 wt %, relative to the weight of the liquid phase, of the dicarboxylic acid salt are suspended in the liquid phase. Following suspension of the salt in the liquid phase, the sludge is ground. For disintegration serve, for example, common mortar grinders, ultrasound or a ball mill or other common wet grinding or disintegration processes. In that, the dicarboxylic acid salt is preferably disintegrated to a particle size of below 1 to 500 nm, in particular 5 to 200 nm. Following disintegration in the liquid phase, the nanoscale dicarboxylic acid salt forms a stable dispersion, in which agglomerates of more than 1000 nm are only present in low amounts or no longer at all. The transition to the nanoscale dispersed phase also shows in the fact that, prior to grinding following suspension in the liquid phase, the suspended dicarboxylic acid salt first directly sediments again, e.g. within a few minutes, but following grinding forms a stable, milky, turbid dispersion, in which the particles do not sediment anymore. This dispersion is thus substantially stable over a usual period of time up to processing, e.g. for a duration of at least one or even several hours. As necessary, the sludge may additionally be filtrated in order to separate such agglomerates, which may still be present following grinding. The filter medium is selected such that all particles with a size >1 µm are separated and subsequently the sludge is free from particles of this size or thereof at least contains less than 1%.

This stable dispersion may be admixed and dried directly with the polypropylene, e.g. in the form of powder or granulate. Alternatively, the liquid phase of the dispersion is separated, and the powder of nanoscale dicarboxylic acid salt thus obtained is admixed with polypropylene in the form of powder or granulate. Via these two possible process variants, a pre-mixture of nanoscale dicarboxylic acid salts and polypropylene is obtained. In both methods, the separation of the non-aqueous, liquid phase is undertaken using common suitable means, for example by evaporation, sucking off in vacuum, distilling off or using a filter press. The pre-mixtures generally contain 0 to 2 wt % of the liquid phase, preferably >0 to 1 wt %.

As necessary, for an even better avoidance of agglomeration of the nanoscale dicarboxylic acid salts and for improvement of dispersibility of the dicarboxylic acid salts in the polypropylene matrix, either upon producing the dispersion or upon mixing the dicarboxylic acid salts with polypropylene, a surfactant, like e.g. higher-value carboxylic acids, silanes, amines or sulfonates, may additionally be added. Particularly preferred for these purposes are long-chain fatty acids, like oleic acid or stearic acid. Surprisingly, the dispersion according to the invention, however, is also largely stable without such aids.

Subsequently, these pre-mixtures of polypropylene and dicarboxylic acid salt may be directly processed into products, wherein, as necessary, further polyolefines and/or further additives may be added. In a preferred variant, in a further process step, these pre-mixtures are compounded into granules with nanoscale dicarboxylic acid salts. The production of the compound is commonly undertaken by melting the pre-mixture at suitable temperatures, for example in a range from 160 to 300° C. Melting preferably takes place in a suitable extruder, for example in a twin-screw extruder, which simultaneously guarantees a good mixture of the nanoscale dicarboxylic acid salt in the polypropylene. The molten mixture is extruded into granules and these cooled at suitable temperatures. During compounding, in addition to the polypropylene, further additives and/or other polyolefines may likewise be added, for example polyethylenes. These compounds are then used for production of the products, for example injection-molded parts, films, porous films, fibers, etc.

In general, the pre-mixtures, or the compounds granulated therefrom, respectively, contain 0.0001 to 5 wt %, preferably 0.001 to 3 wt % of nanoscale, aliphatic dicarboxylic acid salts. In particular for film applications, a content from 0.001 to 1 wt % of dicarboxylic acid salts in the compound or in the pre-mixture, respectively, is preferred. The details in wt % respectively refer to the weight of the mixture or the compound, respectively. As necessary, various dicarboxylic acid salts may also be mixed and subsequently used.

The pre-mixtures of the compounds of at least one polypropylene and nanoscale dicarboxylic acid salts, which are used for producing the products, in general contain at least 50 to <100 wt %, preferably 60 to 99 wt %, in particular 70 to 99 wt %, of a polypropylene and, as necessary, further polyolefines, like e.g. polyethylenes and/or further additives. The details in wt % respectively refer to the weight of the mixture.

Suitable polypropylenes are, for example, isotactic propylene homopolymers with a melting point from 140 to 170° C., preferably from 155 to 168° C., and a melt flow index (measurement according to DIN 53 735 at a load of 21.6 N and 230° C.) from 1.0 to 50 g/10 min, preferably from 1.5 to 20 g/10 min. The n-heptane soluble portion of the polymer in general amounts to 1 to 10 wt %, preferably 2 to 5 wt % relative to the initial polymer. The molecular weight distribution of the propylene polymer may vary.

The ratio of the weight average $M_w$ to the number average $M_n$ in general lies between 1 and 15, preferably at 2 to 10, particularly preferred at 2 to 6. Such a close molecular weight distribution of the propylene homopolymer is achieved, for example, by its peroxide degradation or by production of the polypropylene using suitable metallocene catalysts.

In a further embodiment of the invention, the propylene homopolymer used is highly isotactic. For such highly isotactic polypropylenes, the chain isotactic index of the n-heptane insoluble portion of the polypropylene determined using $^{13}$C-NMR spectroscopy amounts to at least 95%, preferably 96 to 99%.

Furthermore, mixed propylene polymers are suitable as polypropylenes, which in general contain at least 80 wt %, preferably 90 to <100 wt %, in particular 95 to 99 wt % of propylene units. The respective comonomer content of 20 wt %, at most, or >0 to 10 wt % or 1 to 5 wt %, respectively, in general consists, if present, of ethylene and/or butylene. The details in wt % respectively refer to the propylene polymer. Suitable mixed polymers, which contain, e.g., ethylene and/or butylene as comonomer, preferably are statistic mixed polymerisates or block copolymers.

According to the method according to the invention for producing polypropylene with an increased portion of β-crystalline polypropylene, the pre-mixture of polypropylene and nanoscale dicarboxylic acid salts or the compound is molten at suitable temperatures. In general, this temperature lies in a range from 160 to 300° C. Melting preferably takes place in a suitable extruder, for example in a twin-screw extruder, which simultaneously guarantees a good mixture of the nanoscale dicarboxylic acid salt in the polypropylene. The molten mixture is extruded and cooled at suitable temperatures.

The pre-mixture as well as the compounds can be used in the method according to the invention together with further polypropylenes without nucleating agent and/or, as necessary, with further polyolefines and/or additives. All components are then molten together in any extrusion tool or in a kneader and mixed with one another and extruded into products with a portion of β-crystalline polypropylene.

For all process variants, it is essential to the invention that following extrusion, the cooling of the melt, which contains nanoscale dicarboxylic acid salts, is undertaken such that the β-nucleating effect of the nanoscale dicarboxylic acid salts sets in. For that, it is preferred to slowly cool the melt at a temperature in a range from 60 to 135° C., preferably at 80 to 130° C. The closer this temperature is to the crystallization temperature of the β-crystalline polypropylene, the more favorable are the conditions for the formation of the β-crystalline modification. In this manner, via the selection of the temperature upon cooling, a more or less high portion of β-polypropylene can be generated. In addition, the retention period of the cooling melt at the respective temperature has an influence on the β-portion achieved. In order to achieve the highest-possible β-portion, the melt should be cooled very slowly at the higher temperatures, wherein the required retention period at the given temperature in the individual case depends on the shaping upon extrusion.

Depending on the actual application, lower β-portions in the polypropylene may also be sufficient. The β-nucleating dicarboxylic acid salts have a positive effect in these cases, since the cooling rate can be increased, i.e. faster line or extrusion speeds may be used. The β-portion ($1^{st}$ heating) of the propylene produced according to this method may thus, depending on the application, vary in the range of 10-95%, preferably 20-80%, in particular 50-90%.

Using the method according to the invention, under respective cooling conditions, it is possible to achieve a content of β-polypropylene of >80%, preferably 85 to 95% (DSC method, $1^{st}$ heating). For example, via DSC measurements ($1^{st}$ heating) on isotactic propylene homopolymer with 0.1 wt % of nanoscale dicarboxylic acid salts, a portion of β-crystalline polypropylene of 92% was determined.

The method according to the invention may be advantageously applied for the production of films, moldings, in particular tubes and hoses, fibers and other extrusion products. The high efficiency of the nanoscale β-dicarboxylic acids has a beneficial effect in the most different extrusion applications, for example since the extrusion temperature can be reduced or the retention period can be shortened. For some applications, an increased portion of β-crystalline polypropylene is advantageous, since herewith performance characteristics of the polypropylene are improved, e.g. a higher impact strength and stress cracking resistance of the polypropylene is achieved. In a further application, the particularly high β-portion in the polypropylene is used for producing porous films by converting the β-modification into the alpha-modification upon stretching films or in order to generate rough surfaces of a stretched film.

It has been found out that the nanoscale dicarboxylic acid salt offers surprising advantages for the use in a method for producing a porous, biaxially stretched film or also a stretched film with one or several porous layers. On the one hand, the high contents of β-polypropylene have a positive effect on the porosity of this film or the porous layer, respectively, and its gas permeability. However, it was also found out that other β-nucleating agents may result in comparatively high β-contents in the pre-film, for example also dicarboxylic acid salts, which upon production are not subjected to the additional grinding of the sludge. However, it shows that upon using the same, the polypropylene cannot be stretched in the same manner into films or layers, respectively, with high porosities. Upon using the nanoscale dicarboxylic acids according to the invention, stretching conditions, in particular high stretching factors, may be applied, which result in a particularly high porosity of the film or the layer, respectively, wherein simultaneously a surprisingly good operational reliability of the film is given.

The invention is advantageous for producing single-layer and multi-layer porous films. A membrane film is characterized by the fact that it only comprises one, or in case of several layers, only porous layers and has high gas permeability. As necessary, the invention may also be used for a multi-layer film, which beside one or several porous layer/s also comprises one further or several substantially gas-impermeable layer/s. The details in this description relative to the porous film thus accordingly apply in the same manner or analogously also to the porous layer or the porous layers of a multi-layer film.

In particular, upon producing a biaxially stretched polypropylene film, the components of the porous layer or layers, i.e. the mixture or the compound of the nano-dicarboxylic acid salt and polypropylene, as necessary mixed with further polypropylene and/or further polymers and/or further additives, is molten in an extruder at a temperature of at least 160° C. The single- or multi-layer polymer melt is co-/extruded through a flat nozzle, taken up by a receiving roller and cooled on the receiving roller such that the melt solidifies into a pre-film and the desired portion of β-crystalline polypropylene is formed. This cooling of the melt takes places as described above already in a temperature range of preferably 80 to 130° C., wherein a long retention period at this temperature contributes to an increased β-polypropylene portion. For producing a porous film or layer, respectively, in general, a portion of at least 40%, preferably 60 to 95% of β-polypropylene in the pre-film (measured according to DSC, $1^{st}$ heating) is being aimed at, whereas for producing surface roughnesses, lower portions of, for example, 10 to 40% may be sufficient. Subsequently, the pre-film is heated in a per se known manner and stretched in the longitudinal direction, preferably at a temperature of less than 140° C., in particular 80 to 125° C. and with a stretching factor of 2.5:1 to 6:1. Following longitudinal stretching, the longitudinally stretched film is heated again and stretched in the transverse direction, preferably at a temperature of more than 110° C., in particular from 120 to 145° C. and with a stretching ratio from 3:1 to 8:1. With the selected temperatures upon stretching, the β-crystalline polypropylene of the pre-film is converted into the alpha-modification of the polypropylene and, depending on the procedural conditions and the β-portion in the pre-film, generates a continuously porous network-like structure in the film or in the porous layer, respectively, or at least a surface roughness with crater-like depressions, which are formed during the conversion processes. Such rough surface structures are, for example, desired for films with a paper-like character or for capacitor films, which are used as dielectric in capacitors. In order not to impair the electric properties of such capacitor films, it is preferred to use the nanoscale dicarboxylic acid salt in the cover layer/s only, which are to have the surface roughness. It has been found out that the nanoscale dicarboxylic acid salts do not or only slightly impair the electric properties of the capacitor film.

Surprisingly, the film or the layer, respectively, produced with the nanoscale dicarboxylic acid salts according to the invention, has a very high and uniform porosity and a good mechanical stability. The uniform distribution of the pore size is very well noticeable in REM images. The mean pore diameter (bubble point) lies in the range from 50 to 350 nm, preferably in the range from 60 to 300 nm. Upon producing the porous film or the film with a porous layer, respectively, there are only very rarely tear-offs, i.e. the method has a high operational reliability. The film can be stretched with very high factors, so that extraordinarily high porosities can be achieved. In principle, the Gurley value of the various embodiments of the film can vary in a wide range. For such films only comprising porous layers and which, for example, are used as membrane films, the Gurley value in general lies in a range of 100-5000 s, preferably 100 to 2000 s. Surprisingly, according to the present invention, with high stretching factors, porous films with very low Gurley values from 10 to <100 s, preferably 15 to 80 s, in particular 15 to 50 s can also still be reliably produced. Such low Gurley values of below 50 s cannot be achieved with any known methods according to the state of the art. Porous films with Gurley values <600 s and porosities >50% with a thickness of below 30 µm, preferably 10-25 µm, in particular 12-20 µm, can also still be produced with operational reliability.

In a further embodiment, the porous film or the porous layer/s of the film, respectively, in addition to the nanoscale dicarboxylic acid salts and the polypropylenes described above, contain/s as an additional component a propylene block copolymer as well as, as necessary, further polyolefines, which do not impair porosity. In these embodiments, the film or the porous layer, respectively, in general contains 50 to 85 wt %, preferably 60 to 75 wt % of propylene homopolymers and 15 to 50 wt % of propylene block copolymers, preferably 25 to 40 wt %, and 0.001 to 5 wt %, preferably 50-10,000 ppm of the nanoscale dicarboxylic acid salt as β-nucleating agent, relative to the weight of the porous layer or relative to the weight of the film, respectively. As necessary, in addition, common additives are contained in low quantities of below 2 wt %, for example stabilizers and neutralization agents. In case further polyolefines are contained, the portion of the propylene homopolymer or the block copolymer is respectively reduced. In general, the amount of the additional polymers is 0 to <50 wt %, preferably 0.5 to 40 wt %, in particular 1 to 30 wt %, should these be contained in addition. In these cases, the portion of polypropylenes or propylene block copolymers described above is respectively lowered. It applies in the same manner, that said propylene polymer or propylene block copolymer portion is reduced, should higher amounts of up to 2 wt % of nucleating agent be used.

The porous film can be single-layer or multi-layer. The thickness of the porous film in general lies in a range from 10 to 200 µm, preferably 15 to 150 µm, in particular 15 to 100 µm. The density of the porous film in general lies in a range from 0.1 to 0.6 g/cm³, preferably 0.2 to 0.5 g/cm³. The porous film can be provided with a corona, flame or plasma treatment in order to improve filling with electrolytes. As necessary, the micro-porous film may comprise a switch-off layer, which reduces the permeability of the film at increased temperatures.

The porous films may advantageously be used as membranes, for example in batteries, secondary batteries, in supercapacitors or in similar applications.

For characterizing the raw materials and films, the following measuring methods were used:

Melt Flow Index

The melt flow index of propylene polymers was measured according to DIN 53 735 at a load of 2.16 kg and 230° C., and at 190° C. and 2.16 kg for polyethylene.

Melting Points

For the DSC measurement, the polymer was supplied with an amount of heat per time unit with a defined heating rate and the heat flow applied against the temperature. The melting point in terms of the present invention is the maximum of the DSC curve. For determination of the melting point, the DSC curve is recorded with a heating and cooling speed of 10 K/1 min in the range from 20 to 200° C. For determination of the melting point of the polymers, the second heating curve is evaluated, as usual.

Density

The density p is determined according to DIN 53 479, Method A.

Porosity

The porosity is calculated from the density $p_F$ determined at the porous film and the density of the initial raw material polypropylene as follows:

$$P[\%]=100\times(1-\rho_F)/\rho_{PP}$$

In that, for polypropylene, a density of 0.92 g/cm³ was assumed.

Permeability (Gurley Value)

The permeability of the films was measured with the Gurley Tester 4110, according to ASTM D 726-58. In that, the time (in sec) was determined, which 100 cm³ of air need to permeate through the label area of 1 inch² (6.452 cm²). In that, the difference in pressure across the film corresponds to the pressure of a water column with a height of 12.4 cm. The time required then corresponds to the Gurley value.

β-Content

The portion of the β-crystalline polypropylene is determined using DSC. This characterization is described by Varga in J. o. Appl. Polymer Science, Vol. 74, p.: 2357-2368, 1999, and undertaken as follows: in the DSC, the sample with the β-nucleator added is first heated to 220° C. with a heating rate of 20° C./min and molten (1$^{st}$ heating). Thereafter, it is cooled to 100° C. with a cooling rate of 10° C./min, before it is re-molten with a heating rate of 10° C./min (2$^{nd}$ heating).

From the DSC curve of the 1$^{st}$ heating, from the ratio of the melting enthalpies of the β-crystalline phase ($H_\beta$) to the sum of the melting enthalpies of the β- and α-crystalline phases ($H_\beta+H_\alpha$), the degree of crystallinity $K_{\beta,DSC}$ (portion of β-crystalline polypropylene) is determined, which is present in the measured sample (non-oriented film, injection-molded part). The percentage value is calculated as follows:

$$K_{\beta,DSC}[\%]=100\times(H_\beta)/(H_\beta+H_\alpha)$$

From the DSC curve of the 2$^{nd}$ heating, from the ratio of the melting enthalpies of the β-crystalline phase ($H_p$) to the sum of the melting enthalpies of the β- and α-crystalline phases ($H_p+H_a$), the degree of crystallinity $K_{\beta,DSC}$ (2$^{nd}$ heating) is determined, which states the β-portion of the respective polypropylene sample, which can be maximally achieved.

Agglomerates and Particle Size

The particle size of the dicarboxylic acid salts and the presence of agglomerates are determined on raster electron microscope (REM) images of the sample.

For taking the REM images at a film sample, a piece of 5×5 mm is cut from the biaxially stretched film and adhered to the sample carrier. Subsequently, in a sputter unit, a layer of a precious metal (Pt, Au, Pd) with a thickness of a few nanometers is applied to the surface of the film.

The sputtered sample is then introduced into the REM via a lock and there under high vacuum scanned with an acceleration voltage of several kV. The acceleration voltage is selected such that a sharp image results, without the film matrix deforming due to the thermal load. The particles are noticeable in the image that well that the size of the individual particles can be measured using the scale.

The respective determination of the particle size of the dicarboxylic acid salts in the compound is undertaken on a cast film as the test specimen. For that, an approx. 120 to 150 µm non-oriented cast film is produced from the compound. The test with this cast film is undertaken as described above.

The film or the compound, respectively, in terms of the present invention is free from agglomerates, when in the REM image of the film sample no particles with a size of more than 1 µm are found or when a maximum of one particle >1 µm is present. The mean particle size can be obtained by measuring the particle size of a statistically sufficient number of particles. Accordingly, the portion of agglomerates >1 µm may also be determined on the basis of the REM images.

For determination of the particle size of the dicarboxylic acid salts in dispersion, a small amount of the dispersion is applied onto an object slide, dried and likewise sputtered. Of this sputtered sample, a REM image can be taken and the particle size determined. On this sample thus prepared, the presence of agglomerates is examined as well.

The invention is now explained in more detail on the basis of examples:

EXAMPLE 1

An aqueous solution of 40 g pimelic acid in 1000 ml of water was prepared and heated to 83° C. until the pimelic acid was completely dissolved. To this solution, an aqueous calcium hydroxide milk (18.4 g of Ca(OH)$_2$ in 200 ml of water) was added under stirring, whereby calcium pimelate precipitated as a white precipitate. The sedimented precipitate was sucked off and pre-dried at 130° C. in the drying cabinet. Concludingly, the residual moisture and water of crystallization were removed in a vacuum drying cabinet at 200° C. for 24 h. In this manner, a coarse-grained dried powder of calcium pimelate was obtained.

100 g of this dried calcium pimelate were suspended in 500 ml of anhydrous (water content <1 wt %) isopropanol, and the slurry put in a ball mill and milled. In that, a stable milky dispersion was formed. REM images show a particle size of the particles in the dispersion in the range of 75 nm. In the samples, no agglomerates with a particle size of more than 0.8 µm were found.

EXAMPLE 1a

The milky dispersion according to example 1 was dried under exclusion of moisture at 90° C. for 10 h in the exhaust-air dryer. A white powder of nanoscale calcium pimelate was obtained. This powder, at a concentration of 0.4 wt % relative to the polypropylene, was admixed in the mixer with granulate of isotactic polypropylene homopolymer (melting point 162° C.; MFI 3 g/10 min). This mixture was molten in a twin-screw extruder (housing temperature of 240° C. and 200 1/min$^{-1}$) and granulated into rod-shaped grains.

REM images of the granulate grains (test specimen cast film) show the finely distributed agglomerate-free calcium pimelate in the PP matrix. In the REM images, no particles with a size >1 µm were found. Using DSC analysis, the compound of polypropylene and nanoscale calcium pimelate shows a β-value of 97% for the 2$^{nd}$ heating.

EXAMPLE 1b

The milky dispersion according to example 1 was directly tumbled onto a granulate of isotactic polypropylene homopolymer and this mixture dried during tumbling (or subsequently). Following drying, the granulate grains are coated with a layer of nanoscale calcium pimelate and show a milky white color.

REM images of these granulate grains (test specimen cast film) show finely distributed agglomerate-free calcium pimelate on the surface of the granulate grains. These coated granulate grains were molten in a twin-screw extruder (housing temperature 240° C. and 200 1/min$^{-1}$) and granulated into rod-shaped grains. Using DSC analysis, this compound of polypropylene and nanoscale calcium pimelate likewise shows a β-value of 97% for the 2$^{nd}$ heating. REM images of these granulate grains show the Ca-pimelate particles finely distributed with a size of <100 nm. In the REM images, no particles with a size >1 μm were found.

COMPARATIVE EXAMPLE 1

An aqueous solution with 40 g of pimelic acid in 1000 ml of water was prepared and heated to 83° C. until the pimelic acid was completely dissolved. To this solution, an aqueous calcium hydroxide solution (18.4 g Ca(OH)$_2$ in 200 ml) was added under stirring, whereby calcium pimelate was precipitated as a white precipitate. The sedimented precipitate was sucked off and pre-dried at 130° C. in the drying cabinet. Concludingly, the residual moisture and water of crystallization were removed in a vacuum drying cabinet at 200° C. for 24 h. In this manner, a coarse-grained dried powder of calcium pimelate was obtained.

100 g of this dried calcium pimelate were put in a ball mill and milled in the dry state. A white powder of calcium pimelate was obtained. REM images show a grain size of the powder in the range of 500 nm with agglomerates, the particle size of which is up to 2 μm.

COMPARATIVE EXAMPLE 1a

The powder according to comparative example 1, at a concentration of 0.4 wt %, was admixed in the mixer with granulate of isotactic polypropylene homopolymer (melting point 162° C.; MFI 3 g/10 min). This mixture was molten in a twin-screw extruder (housing temperature of 240° C. and 200 1/min$^{-1}$) and granulated into rod-shaped grains.

REM images of the granulate grains (test specimen cast film) show the finely distributed calcium pimelate in the PP matrix, however, agglomerates with a particle size from 1 to 10 μm are present as well. Using DSC analysis, the mixture of polypropylene and nanoscale calcium pimelate shows a β-value of 97% for the 2$^{nd}$ heating.

FILM EXAMPLE 1

In a mixer, the compound according to example 1a was admixed with propylene homopolymer and propylene block copolymer. This mixture was molten in an extruder and further homogenized. Following the extrusion process, the melt was extruded from a flat film die at an extrusion temperature of 245° C. into a single-layer film. This film had the following composition:
approx. 50 wt % propylene homopolymer (PP) with a n-heptane soluble portion of 4.5 wt % (relative to 100% PP) and a melting point of 165° C.; and a melt flow index of 3.2 g/10 min at 230° C. and a load of 2.16 kg (DIN 53 735) and
approx. 49.96 wt % propylene ethylene block copolymer with an ethylene portion of approx. 5 wt % relative to the block copolymer and a melt flow index (230° C. and 2.16 kg) of 6 g/10 min 0.04 wt % nano-Ca-pimelate as β-nucleating agent
The film additionally contained a stabilizer and a neutralization agent in common quantities.

Following extrusion, the polymer mixture was led over a first feed roller and a further roller triplet, cooled and solidified, subsequently stretched in the longitudinal direction, stretched in the transverse direction and fixed, wherein in detail, the following conditions were chosen:
Extrusion: Extrusion temperature 245° C.
Cooling roller: Temperature 125° C.
Line speed: 1.5 m/min (retention period on the feed roller: 55 sec)
Longitudinal stretching: Stretch roller T=90° C.
Longitudinal stretching by Factor 4
Transverse stretching: Heating fields T=145° C.
Stretch fields T=145° C.
Transverse stretching by Factor 4

The porous film thus produced had a thickness of approx. 30 μm, a density of 0.30 g/cm$^3$ and a uniform white-opaque appearance. The porosity amounted to 66% and the Gurley value was 340 s. In film production, there were no tear-offs over several hours. The REM image (FIG. 1) shows a uniform distribution of the Ca-pimelate without agglomerates in the porous film. The dicarboxylic acid salts are well recognizable as light spots on the polymer strands of the polypropylene network.

FILM EXAMPLE 2

A film was produced like described in film example 1. Differing from film example 1, the compound according to example 1b was now used. A film with the same properties like according to example 1 was obtained. Likewise, there were no tear-offs during production.

FILM EXAMPLE 3

A film was produced like described in film example 2. The composition remained unchanged. Differing from film example 1, upon production, stretching was undertaken with a longitudinal stretch factor of 4.8 and for transverse stretching with a factor 5.8. The porous film thus produced had a thickness of approx. 20 μm, a density of 0.25 g/cm$^3$ and a uniform white-opaque appearance. The porosity amounted to 60% and the Gurley value was 200 s. Likewise, there were no tear-offs during production.

FILM EXAMPLE 4

A film was produced like described in film example 3. The composition remained unchanged. Differing from film example 1, upon production, a lower line speed of 1 m/min (retention period on the feed roller: 80 sec) was chosen. The remaining procedural conditions remained unchanged. The porous film thus produced had a thickness of approx. 25 μm, a density of 0.25 g/cm$^3$ and a uniform white-opaque appearance. The porosity amounted to 70% and the Gurley value was 60 s. Production of this film was surprisingly reliable, too.

COMPARATIVE EXAMPLE 1

Film

A film was produced like described in film example 1. However, differing from film example 1, a compound produced according to comparative example 1a was used. A film with a similar property profile was obtained. However, in the course of 4 production hours, there were 5 tear-offs. REM images of the biaxially stretched film show agglomerated particles with a size of up to 5 μm.

COMPARATIVE EXAMPLE 2

Figure 2:
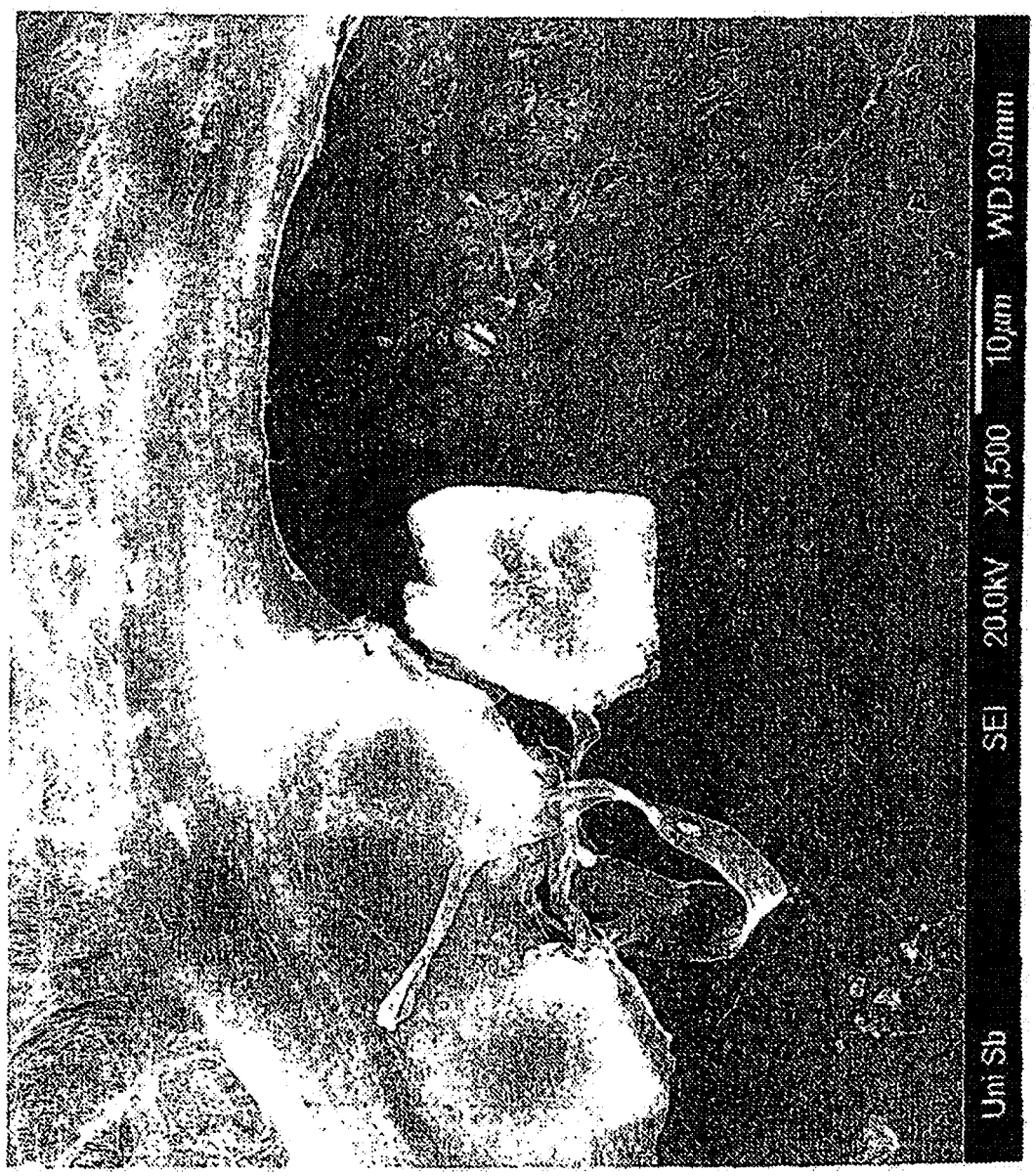
FIG. 2 shows agglomerated particles with a size of up to 5 µm and more.

A film like in film example 3 was produced. However, differing from film example 3, a compound produced according to comparative example 1a was used. A film with a similar property profile like according to film example 3 was obtained. However, in the course of 4 production hours, there were 10 tear-offs. De facto, the film could not be reliably produced and was uneconomical. REM images (FIG. 2) show agglomerated particles with a size of up to 5 µm and more. In FIG. 2, it is particularly well noticeable, how these agglomerates generate tear-ups upon stretching, which then result in tear-offs during production.

COMPARATIVE EXAMPLE 3

It was attempted to produce a film like in film example 4. However, differing from film example 4, a compound produced according to comparative example 1a was used. Using these procedural conditions, due to permanent tear-offs, no film could be produced.

EXAMPLE 2

An aqueous solution of 40 g suberic acid in 1000 ml of water was prepared and heated to 85° C. until the suberic acid was completely dissolved. To this solution, an aqueous calcium hydroxide milk (17.02 g of $Ca(OH)_2$ in 200 ml of water) was added under stirring, whereby calcium suberate precipitated as a white precipitate. The sedimented precipitate was sucked off and pre-dried at 130° C. in the drying cabinet. Concludingly, the residual moisture and water of crystallization were removed in a vacuum drying cabinet at 200° C. for 24 h. In this manner, a coarse-grained dried powder of calcium suberate was obtained.

100 g of this dried calcium suberate were suspended in 300 ml of anhydrous isopropanol, and the slurry put in a ball mill and milled. In that, a stable milky dispersion was formed. REM images show a particle size of the particles in the dispersion in the range of 75 nm. In the samples, no agglomerates with a particle size of more than 1 µm were found.

EXAMPLE 2a

Powder

The milky dispersion according to example 2 was dried under exclusion of moisture at 90° C. for 10 h in the exhaust-air dryer. A white powder of nanoscale calcium suberate was obtained.

This powder, at a concentration of 0.4 wt % relative to the polypropylene, was admixed in the mixer with granulate of isotactic polypropylene homopolymer (melting point 162° C.; MFI 3 g/10 min). This mixture was molten in a twin-screw extruder (housing temperature of 240° C. and 200 $1/min^{-1}$) and granulated into rod-shaped grains.

REM images of the granulate grains (test specimen cast film) show the finely distributed agglomerate-free calcium suberate in the PP matrix. Using DSC analysis, the mixture of polypropylene and nanoscale calcium suberate shows a β-value of 99% for the $2^{nd}$ heating.

EXAMPLE 2b

The milky dispersion according to example 2 was directly tumbled onto a granulate of isotactic polypropylene homopolymer and this mixture dried during tumbling (or subsequently). Following drying, the granulate grains are coated with a layer of nanoscale calcium suberate and show a milky white color.

REM images of these granulate grains (test specimen cast film) show finely distributed agglomerate-free calcium suberate on the surface of the granulate grains. These coated granulate grains were molten in a twin-screw extruder (housing temperature 240° C. and 200 $1/min^{-1}$) and granulated into rod-shaped grains. Using DSC analysis, this compound of polypropylene and nanoscale calcium suberate likewise shows a β-value of 99% for the $2^{nd}$ heating. REM images of the granulate grains (test specimen cast film) show the Ca-suberate particles finely distributed with a size of <100 nm. No agglomerates with a particle size >1 µm are present.

FILM EXAMPLE 5

In a mixer, the compound according to example 2a was admixed with propylene homopolymer and propylene block copolymer. This mixture was molten in an extruder and further homogenized. Following the extrusion process, the melt was extruded from a flat film die at an extrusion temperature of 245° C. into a single-layer film. This film had the following composition:

approx. 50 wt % propylene homopolymer (PP) with a n-heptane soluble portion of 4.5 wt % (relative to 100% PP) and a melting point of 165° C.; and a melt flow index of 3.2 g/10 min at 230° C. and a load of 2.16 kg (DIN 53 735) and approx. 49.96 wt % propylene ethylene block copolymer with an ethylene portion of approx. 5 wt % relative to the block copolymer and a melt flow index (230° C. and 2.16 kg) of 6 g/10 min 0.04 wt % nano-Ca-suberate as β-nucleating agent The film additionally contained a stabilizer and a neutralization agent in common quantities.

Following extrusion, the polymer mixture was led over a first feed roller and a further roller triplet, cooled and solidified, subsequently stretched in the longitudinal direction, stretched in the transverse direction and fixed, wherein in detail, the following conditions were chosen:

Extrusion: Extrusion temperature 245° C.
Cooling roller: Temperature 125° C.
Line speed: 1.5 m/min (retention period on the feed roller: 55 sec)
Longitudinal stretching: Stretch roller T=90° C.
Longitudinal stretching by Factor 4
Transverse stretching: Heating fields T=145° C.
Stretch fields T=145° C.
Transverse stretching by Factor 4

The porous film thus produced had a thickness of approx. 30 µm, a density of 0.30 g/cm³ and a uniform white-opaque appearance. The porosity amounted to 66% and the Gurley value was 340 s. In film production, there were no tear-offs over several hours.

FILM EXAMPLE 6

A film was produced like described in film example 5. Differing from film example 5, the compound according to example 2b was now used. A film with the same properties like according to film example 5 was obtained. Likewise, there were no tear-offs during production.

The invention claimed is:

1. A method for producing a stable dispersion of a non-aqueous, liquid phase and dispersed dicarboxylic acid salts, which comprises reacting an aliphatic dicarboxylic acid with a divalent metal salt in an aqueous solution to form a dicarboxylic acid salt and subsequently separating and drying said dicarboxylic acid salt, wherein said dried dicarboxylic acid salt is elutriated and disintegrated in a non-aqueous, liquid phase, until a stable dispersion is formed.

2. The method according to claim 1, wherein said dicarboxylic acid is an aliphatic dicarboxylic acid with 4 to 15 C-atoms and said non-aqueous, liquid phase is an alcohol.

3. The method according to claim 1, wherein said dicarboxylic acid is pimelic acid or suberic acid.

4. The method according to claim 1, wherein said metal salt is an alkaline earth salt.

5. The method according to claim 1, wherein said metal salt is a hydroxide, a carbonate or a chloride.

6. The method according to claim 1, wherein said liquid phase is an ethanol, butanol or isopropanol and said metal salt is a calcium salt or calcium hydroxide.

7. The method according to claim 1, wherein the water content of said dicarboxylic acid salt after drying amounts to <1 wt %.

8. The method according to claim 1, wherein the water content of said non-aqueous, liquid phase amounts to <1 wt %.

9. The method according to claim 1, wherein 10 to 50 wt % of dicarboxylic acid salt, relative to the weight of said non-aqueous, liquid phase, are suspended.

10. The method according to claim 1, wherein said dispersion contains <1% of dicarboxylic acid salts with a particle size of >1 μm.

11. A method for producing a compound of polypropylene and nanoscale dicarboxylic acid salt, wherein said non-aqueous, liquid phase is removed from said dispersion, produced according to claim 1, the remaining powder of dicarboxylic acid salt is admixed with polypropylene and subsequently the pre-mixture thus obtained is molten and extruded into a granulated compound.

12. The method for producing a compound of polypropylene and nanoscale dicarboxylic acid salt, wherein said dispersion produced according to claim 1, is admixed with polypropylene, said non-aqueous, liquid phase is removed from this mixture and subsequently the pre-mixture thus obtained is molten and extruded into a granulated compound.

13. The method according to claim 11, wherein the mean particle diameter of said dicarboxylic acid salt in said compound is 1 to 500 nm.

14. The method according to claim 11, wherein in said compound, less than 1% particles or agglomerates of said dicarboxylic acid with a particle diameter of >1000 nm are present.

15. The method according to claim 11, wherein said compound contains 0.001 to 5 wt % of dicarboxylic acid salt.

16. The method according to claim 11, wherein said propylene polymer is an isotactic propylene homopolymer and/or a propylene block copolymer.

17. The method according to claim 11, wherein upon compounding, further additives and/or further polyolefines are admixed.

18. The method for producing a polypropylene with an increased portion of β-crystalline polypropylene, wherein a compound, produced according to the method according to claim 11, as necessary mixed with polypropylene and/or a further polymer, is molten at a temperature of at least 150° C. and subsequently cooled such that said cooled polypropylene melt has an increased portion of β-crystalline polypropylene.

19. A method for producing a biaxially stretched polypropylene film with at least one porous layer, wherein a compound, produced according to the method according to claim 11, as necessary mixed with polypropylene and/or further polyolefines and/or further additives, is molten at a temperature of at least 150° C. and extruded trough a flat nozzle and cooled on cooling rollers such that the cooled pre-film has an increased portion of β-crystalline polypropylene and the pre-film is subsequently heated and stretched in longitudinal direction and in transverse direction and wherein the temperature during stretching is selected such that said β-crystalline polypropylene of said pre-film converts into the alpha-modification of the polypropylene.

20. The method according to claim 19, wherein said portion of β-crystalline polypropylene in said pre-film amounts to 60 to 95% (1st heating).

21. The method according to claim 19, wherein said cooling of said pre-film is undertaken in a temperature range of 100-140° C.

22. The method according to claim 19, wherein said polypropylene of said mixture is an isotactic polypropylene with a melting point in the range of 140 to 170° C.

23. The method according to claim 19, wherein said polypropylene is a mixed polymer with a comonomer portion of ethylene and/or butylene of up to 20 wt %.

24. The method according to claim 19, wherein said polypropylene is a mixture of propylene homopolymer and propylene block copolymer.

25. The method according to claim 19, wherein said nanoscale dicarboxylic acid salt in said porous film has a particle size of less than 100 nm and no agglomerates with a particle size of >1 μm are present.

26. The method according to claim 19, wherein said film has a Gurley value of <500 s.

27. The method according to claim 19, wherein said film has a Gurley value of <100 s.

28. A dielectric in a capacitor which comprises the film which is produced according to the method according to claim 19.

29. A film with paper-like properties which comprises the film which is produced according to the method according to claim 19.

* * * * *